(12) United States Patent
Inagaki et al.

(10) Patent No.: US 7,959,778 B2
(45) Date of Patent: Jun. 14, 2011

(54) SENSOR CONTROL APPARATUS AND METHOD

(75) Inventors: Hiroshi Inagaki, Aichi (JP); Yoshinori Inoue, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1064 days.

(21) Appl. No.: 11/518,945

(22) Filed: Sep. 12, 2006

(65) Prior Publication Data

US 2007/0056860 A1 Mar. 15, 2007

(30) Foreign Application Priority Data

Sep. 13, 2005 (JP) ................................ 2005-264879

(51) Int. Cl.
*G01N 27/406* (2006.01)
(52) U.S. Cl. ........ 204/425; 204/424; 204/426; 204/427; 73/23.31; 73/23.32
(58) Field of Classification Search .......... 204/421–429, 204/406; 205/781, 783.5–785; 123/672–697; 73/23.31–23.32
See application file for complete search history.

(56) References Cited

U.S. PATENT DOCUMENTS

| 5,172,677 | A | * | 12/1992 | Suzuki | ........................ | 123/688 |
| 5,391,284 | A | | 2/1995 | Hotzel | | |
| 5,758,310 | A | | 5/1998 | Kato | | |
| 5,895,564 | A | * | 4/1999 | Miyata et al. | .............. | 205/784.5 |
| 5,974,857 | A | * | 11/1999 | Yamashita et al. | ........... | 73/23.32 |
| 6,332,966 | B1 | * | 12/2001 | Sakai et al. | ................... | 204/425 |

FOREIGN PATENT DOCUMENTS

| EP | 0507149 A1 | 10/1992 |
| EP | 0833148 A2 | 4/1998 |
| JP | 4-313056 A | 11/1992 |
| JP | 9-170997 A | 6/1997 |
| JP | 09-170997 A | 6/1997 |
| JP | 10-104195 A | 4/1998 |
| JP | 2001-241347 A | 9/2001 |
| JP | 2004-69547 A | 3/2004 |

OTHER PUBLICATIONS

Non-Final Office Action, dated Jul. 9, 2010 (in U.S. Appl. No. 11/604,218).

* cited by examiner

*Primary Examiner* — Nam X Nguyen
*Assistant Examiner* — Bach T Dinh
(74) *Attorney, Agent, or Firm* — Sughrue Mion, PLLC

(57) ABSTRACT

A sensor control apparatus comprising an air/fuel ratio sensor having a sensor cell with a pair of electrodes, a current source capable of supplying a predetermined current between the electrodes, a current control section that turns on/off the current source, a voltage detecting section that detects voltages generated between the electrodes at respective times when the current source is turned on and off, a differential voltage detecting section that detects a differential voltage between the voltages that are generated at the respective times when the current source is turned on and off, a first voltage comparing section that compares the differential voltage with a first threshold voltage, and a half-activated state determining section that determines that the sensor cell has reached a half-activated state when the differential voltage is lower than the first threshold voltage. A sensor control method is also provided.

6 Claims, 6 Drawing Sheets

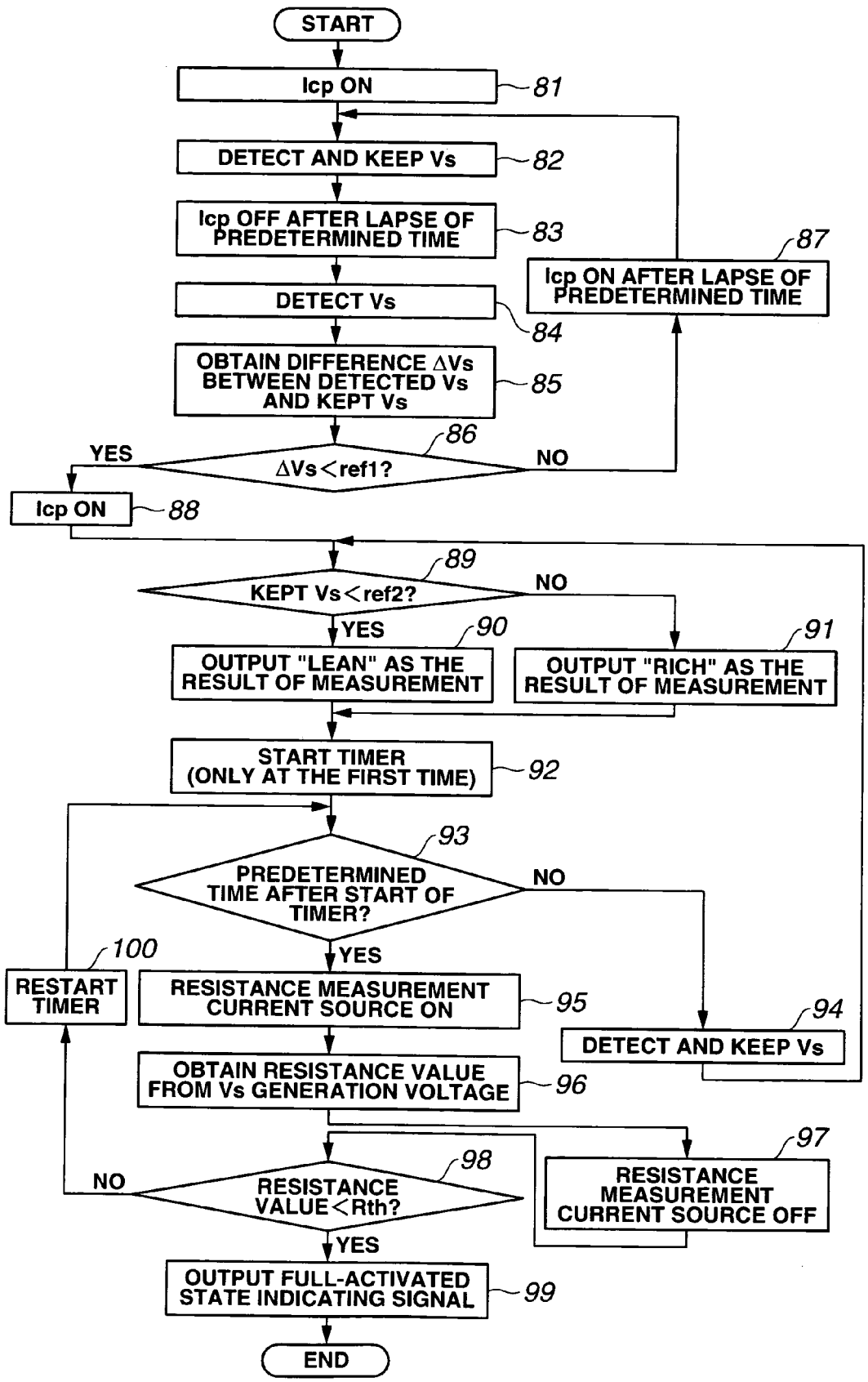

SENSOR CONTROL APPARATUS AND METHOD

BACKGROUND OF THE INVENTION

The present invention relates to a sensor control apparatus and method for controlling an air/fuel ratio sensor that detects a concentration of a particular gas component of an exhaust gas emitted from an internal combustion engine and particularly to a sensor control apparatus and method capable of attaining earlier or accelerated start of an air/fuel ratio control after start of the engine.

For an air/fuel ratio control of an internal combustion engine, a sensor control apparatus having an air/fuel ratio sensor for detecting an oxygen concentration in an exhaust gas emitted from an internal combustion engine (air/fuel ratio) has been put to practical use. Generally known as such an air/fuel ratio sensor are a sensor (so-called λ sensor) that produces a binary output in response to an oxygen concentration in an exhaust gas (i.e., in response to a rich or lean air/fuel ratio) and a sensor (pump current type or limiting current-type oxygen sensor) that produces a nearly linear output over a wide range of oxygen concentration. In recent years, to comply with stringent exhaust gas regulations of an internal combustion engine, it is required to control the air/fuel ratio accurately and therefore a pump current type or limiting current-type oxygen sensor have been used in place of the λ sensor.

In either of the sensors is used, as a principle, a sensor cell having a pair of electrodes on the opposite sides of a solid electrolyte (e.g., $ZrO_2$) so as to utilize such a phenomenon that an electromotive force is produced when the ambient gases on the opposite sides of the sensor cell are different in oxygen concentration and oxygen ion moves between the opposite sides through the solid electrolyte when current is supplied between the electrodes. Such a phenomenon is not attained unless the solid electrolyte is heated and activated. In the meantime, there may occur such a case where it takes a long time from over ten seconds to tens of seconds for the pump current type or the limiting current-type oxygen sensor that can detect an oxygen concentration over a wide range, to become activated.

Generally, a sensor control apparatus is configured to be able to detect whether the sensor has reached an activated condition. The technique for detecting such an activated condition is disclosed in Japanese Unexamined Patent Publication Nos. 4-313056, 10-104195 and 9-170997.

SUMMARY OF THE INVENTION

In the meantime, in recent years, more stringent exhaust gas regulations are required. In case of the pump current type or the limiting current-type oxygen sensor that needs a relatively long time until it reaches an activated state and becomes able to serve as a linear sensor, the sensor is required to serve as a λ sensor that can determine whether an air/fuel ratio of exhaust gas is richer or leaner as compared with a theoretical air/fuel ratio at a stage before the sensor becomes able to serve as a linear sensor, for thereby attaining an earlier or accelerated air/fuel ratio feedback control.

However, the above-described Japanese Unexamined Patent Publications Nos. 4-313056 and 10-104195 relate to a technique for determining whether the sensor (cell) is completely activated (i.e., whether the sensor has reached a full-activated state) and not a technique for determining whether the sensor (cell) has reached a half-activated state that enables the sensor to determine whether the air/fuel ratio of the exhaust gas is rich or lean. On the other hand, Japanese Unexamined Patent Publication No. 9-170997 discloses a technique for estimating a half-activated state of the air-fuel ratio sensor on the basis of an integrated value of output voltage of the air/fuel ratio sensor. However, the output voltage of the air/fuel ratio sensor varies depending upon a variation of the gaseous atmosphere to which the air/fuel ratio sensor is exposed (in other words, the air/fuel ratio state of the gas to be measured). For this reason, by the technique for estimating whether the air/fuel ratio sensor has reached the half-activated state by comparing the integrated value of the output voltage of the air/fuel ratio sensor with a threshold value that is simply determined based on one aspect of a matter, there may possibly occur such a case where the air/fuel ratio sensor is erroneously determined as having reached the half-activated state. Namely, by the technique of Japanese Unexamined Patent Publication No. 9-170997, judgment on the half-activated state of the air/fuel ratio sensor is largely influenced by the gaseous atmosphere to which the air/fuel ratio sensor is exposed, so that accurate detection of the half-activated state of the air/fuel ratio sensor cannot be obtained and accurate feedback control of the air/fuel ratio cannot be realized.

It is accordingly an object of the present invention to provide a sensor control apparatus and method that can detect a concentration of a particular component of an exhaust gas over a wide range and can detect a half-activated state of the air/fuel ratio sensor accurately without being influenced by a gaseous atmosphere to which the air/fuel ratio sensor is exposed so that earlier or accelerated start of an air/fuel ratio feedback control can be attained.

To achieve the above object, there is provided according to an aspect of the present invention a sensor control apparatus comprising an air/fuel ratio sensor having a sensor cell with a pair of electrodes on opposite sides of a solid electrolyte and capable of detecting a concentration of a particular gas component of an exhaust gas emitted from an internal combustion engine, a current source capable of supplying a predetermined current between the pair of electrodes, a current control section that turns on/off the current source at a predetermined cycle, a voltage detecting section that detects voltages generated between the pair of electrodes at respective times when the current source is turned on and off, a differential voltage detecting section that detects a differential voltage between the voltages that are generated at the respective times when the current source is turned on and off and detected by the voltage detecting section, a first voltage comparing section that compares the differential voltage with a first threshold voltage, and a half-activated state determining section that determines that the sensor cell has reached a half-activated state that enables the air/fuel ratio sensor to measure whether an air/fuel ratio of the exhaust gas is rich or lean on the basis of an output of the sensor cell, when the differential voltage is lower than the first threshold voltage.

In the sensor control apparatus, a predetermined current is supplied between the pair of electrodes disposed on the opposite sides of the solid electrolyte while turning on/off the current at a predetermined cycle. The voltages that are produced between the pair of electrodes when the current source is turned on and off are detected by the voltage detecting section. The difference in voltage between the pair of electrodes is little when the sensor cell is in an activated state and considerably large when the sensor cell is in a non-activated state due to a large internal resistance value of the solid electrolyte. On the other hand, the difference in voltage between the pair of electrodes becomes intermediate between little difference and a considerably large difference at the stage of transition from a non-activated state to an activated state.

Thus, by the apparatus, an intermediate difference is detected by the differential voltage detecting section and the first voltage detecting section and it can be known directly from the output of the sensor cell whether the air/fuel ratio sensor has reached the half-activated state. When the air/fuel ratio sensor is in the half-activated state, it becomes possible to allow the air/fuel ratio sensor capable of detecting a concentration of particular gas component of an exhaust gas over a wide range to serve as a sensor (so-called λ sensor) that can produce a binary output in response to a rich or lean air/fuel ratio. Accordingly, by using such an output of the air/fuel ratio sensor, it becomes possible to perform an air/fuel ratio feedback control by using the air/fuel ratio sensor rapidly after start of the internal combustion engine even if the air/fuel ratio sensor has not yet reached the full-activated state. In the meantime, "half-activated state" is herein used to indicate the state before the air/fuel ratio sensor reaches a full-activated state and it can be measure based on the output of the sensor cell whether the air/fuel ratio of the exhaust gas is rich or lean (i.e., the sensor cell can produce a binary output in response to a rich or lean air/fuel ratio of the exhaust gas).

Further, a remarkable point of the sensor control apparatus of the present invention resides in that the differential voltage is detected on the basis of the voltages that are generated at the respective times when the current source is on and off and detected by the voltage detecting section and it is detected on the basis of the differential voltage whether the air/fuel ratio sensor has reached the half-activated state. The voltage value Von generated between the pair of electrodes when the current source in on is obtained from Ipc×RP+EMF (i.e., Von=Ipc×Rp+EMF where Ipc is a current value of the above-described predetermined current, Rp is an internal resistance of the sensor cell and EMF is an electromotive force of the sensor cell), and the voltage value Voff generated between the pair of electrodes when the current source is off is obtained from EMF since the current value of the predetermined current is 0 A (i.e., Voff=EMF). According to the present invention, for determination of whether the sensor cell has reached the half-activated state, it is detected as described above the differential voltage (Von-Voff) and therefore the electromotive force EMF of the sensor cell is offset. While the electromotive force EMF varies depending upon a variation of the gaseous atmosphere to which the air/fuel ratio sensor (sensor cell) is exposed even if the internal resistance of the sensor cell is constant, the influence of the electromotive force EMF (in other words, the influence of the gaseous atmosphere) on the determination of the half-activated state of the sensor cell is eliminated by using the differential voltage for the determination. Thus, according to the present invention, it can be detected accurately whether the sensor call has reached the half-activated state, without being influenced by the gaseous atmosphere to which the sensor cell is exposed.

According to another aspect of the present invention, there is provided a sensor control apparatus further comprising a second voltage comparing section that compares, when it is determined by the half-activated state determining section that the sensor cell has reached the half-activated state, a voltage between the pair of electrodes, which is detected by the voltage detecting section when the current source is on or off, with a second threshold voltage and a rich/lean measurement result output section that outputs a signal indicative of the air/fuel ratio of the exhaust gas being rich or lean on the basis of the result of comparison by the second voltage comparing section. This improves the function of the sensor control apparatus. Further, the signal indicative of whether the air/fuel ratio is rich or lean may be outputted from the rich/lean measurement result determining section during the time after it is determined that the sensor cell has reached the half-activated state and before the sensor cell reaches the full-activated state, by continuing supply of the predetermined current and comparing the voltage across the pair of electrodes with the second threshold voltage by the second voltage comparing section. By this, it becomes possible to attain a good air/fuel ratio feedback control continuously till the sensor cell reaches the full-activated state.

According to a further aspect of the present invention, there is provided a sensor control apparatus further comprising a full-activated state determining section that determines whether the sensor cell has reached a full-activated state on the basis of an information different from the differential voltage after it is determined by the half-activated state determining section that the sensor cell has reached the half-activated state.

It is also possible to determine whether the sensor cell has reached the full-activated state on the basis of the differential voltage. However, for accurately determining whether the sensor cell has reached the half-activated state, it is preferable to set the first threshold voltage at the first voltage comparing section at a relatively small value (namely, a value relatively close to zero). For this reason, if it is tried to determine whether the sensor cell has reached the full-activated state by using the differential voltage, it may possibly be difficult to retain the accuracy in determination of the half-activated state of the sensor cell since the first threshold value must inevitably set at a relatively large value for setting of the threshold voltage for determination of the full-activated state. Thus, by determining whether the sensor cell has reached the full-activated state on the basis of the information different from the differential voltage, it becomes possible to obtain a good accuracy in determination of the half-activated condition of the sensor cell.

In the meantime, the means for determining whether the sensor cell has reached the full-activated state on the basis of the information different from the differential voltage is not limited to particular one but can be, for example in case the air/fuel ratio sensor has a heater, such one that causes the heater to heat in timed relation to start of the sensor control apparatus, calculate the total amount of power consumed by the heater and determine whether the total amount of power has reached a reference total amount of power that is set beforehand. However, in case of determining whether the sensor cell has reached the full-activated state, it is preferable from the point of view of making higher the accuracy in determination to directly use the information concerning the sensor cell similarly to the determination of the half-activated condition.

According to a further aspect of the present invention, there is provided a sensor control apparatus wherein the full-activated state determining section uses an internal resistance value of the sensor cell as the above-described information.

According to a further aspect of the present invention, there is provided a sensor control apparatus further comprising a resistance value detecting section that detects the internal resistance value of the sensor cell, wherein the full-activated state detecting section compares the internal resistance value of the sensor cell with a threshold value and determines that the sensor cell has reached the full-activated state when the internal resistance value is lower than the threshold value. By this, it becomes possible to carry out an air/fuel ratio feedback control on the basis of the voltage between the pair of electrodes after the sensor cell has reached the half-activated state, while being capable of separately detecting whether the sensor cell has reached the full-activated state accurately.

According to a further aspect of the present invention, there is provided a sensor control apparatus wherein the air/fuel ratio sensor further includes a pump cell having a pair of electrodes on opposite sides of a solid electrolyte, one of the electrodes of each of the pump cell and the sensor cell facing a hollow gas detecting chamber into which an exhaust gas is introduced, one of the electrodes of the sensor cell, which is positioned on a side opposite to the gas detecting chamber, being a reference electrode closed to the outside, the sensor control apparatus further comprising a control section that supplies the predetermined current of the current source to the sensor cell in the direction to pump oxygen out of the gas detecting chamber to the reference electrode for thereby allowing the reference electrode to function as an internal reference oxygen source. The current source doubles as a source for supplying a predetermined current to the sensor cell with a view to making the reference electrode of the sensor cell store oxygen of a predetermined concentration and thereby making the same serve as the internal reference oxygen source and a source for supplying a predetermined current to the sensor cell for determination of the half-activated state of the sensor cell. By this, drive of the air/fuel ratio sensor and determination of the half-activated state thereof can be attained without the necessity of a plurality of current sources, thus making it possible to reduce the cost of the sensor control apparatus.

According to a further aspect of the present invention, there is provided a sensor control method for controlling an air/fuel ratio sensor having a sensor cell with a pair of electrodes on opposite sides of a solid electrolyte and capable of detecting a concentration of a particular gas component of an exhaust gas emitted from an internal combustion engine, the method comprising the steps of supplying a predetermined current of a current source between the pair of electrodes while turning on/off the current source at a predetermined cycle, detecting voltages generated between the pair of electrodes at respective times when the current source is turned on and off, detecting a differential voltage between the voltages that are generated between the pair of electrodes at the respective times when the current source is turned on and off and detected by the step of detecting, comparing the differential voltage with a first threshold voltage, and determining that the sensor cell has reached a half-activated state that enables the air/fuel ratio sensor to measure whether an air/fuel ratio of the exhaust gas is rich or lean on the basis of an output of the sensor cell, when the differential voltage is lower than the first threshold voltage. This method can also realize an air/fuel ratio feedback control rapidly after start of the internal combustion engine similarly to the above-described sensor control apparatus.

According to a further aspect of the present invention, there is provided a sensor control method further comprising the steps of comparing, when it is determined by the step of determining that the sensor cell has reached the half-activated state, a voltage generated between the pair of electrodes when the current source is on or off, with a second threshold voltage, and outputting a signal indicative of whether the air/fuel ratio of the exhaust gas is rich or lean, on the basis of the result of comparison by the step of comparing the voltage between the pair of electrodes with the second threshold voltage.

According to a further aspect of the present invention, there is provided a sensor control method further comprising a step of determining whether the sensor cell has reached the full-activated state on the basis of an information different from the differential voltage after it is determined by the step of determining that the sensor cell has reached the half-activated state.

According to a further aspect of the present invention, there is provided a sensor control method wherein the step of determining whether the sensor cell has reached the full-activated state comprises using an internal resistance value of the sensor cell as the above-described information.

According to a further aspect of the present invention, there is provided a sensor control method further comprising a step of detecting the internal resistance value of the sensor cell, wherein the step of determining whether the sensor cell has reached the full-activated state comprises comparing the internal resistance value of the sensor cell with a threshold value and determining that the sensor cell has reached the full-activated state when the internal resistance value is lower than the threshold value.

BRIEF DESCRIPTION OF THE DRAWINGS

FIG. 6 is a flow chart showing an operation of the sensor control apparatus of FIG. 1.

DESCRIPTION OF THE PREFERRED EMBODIMENT

Figure 1:
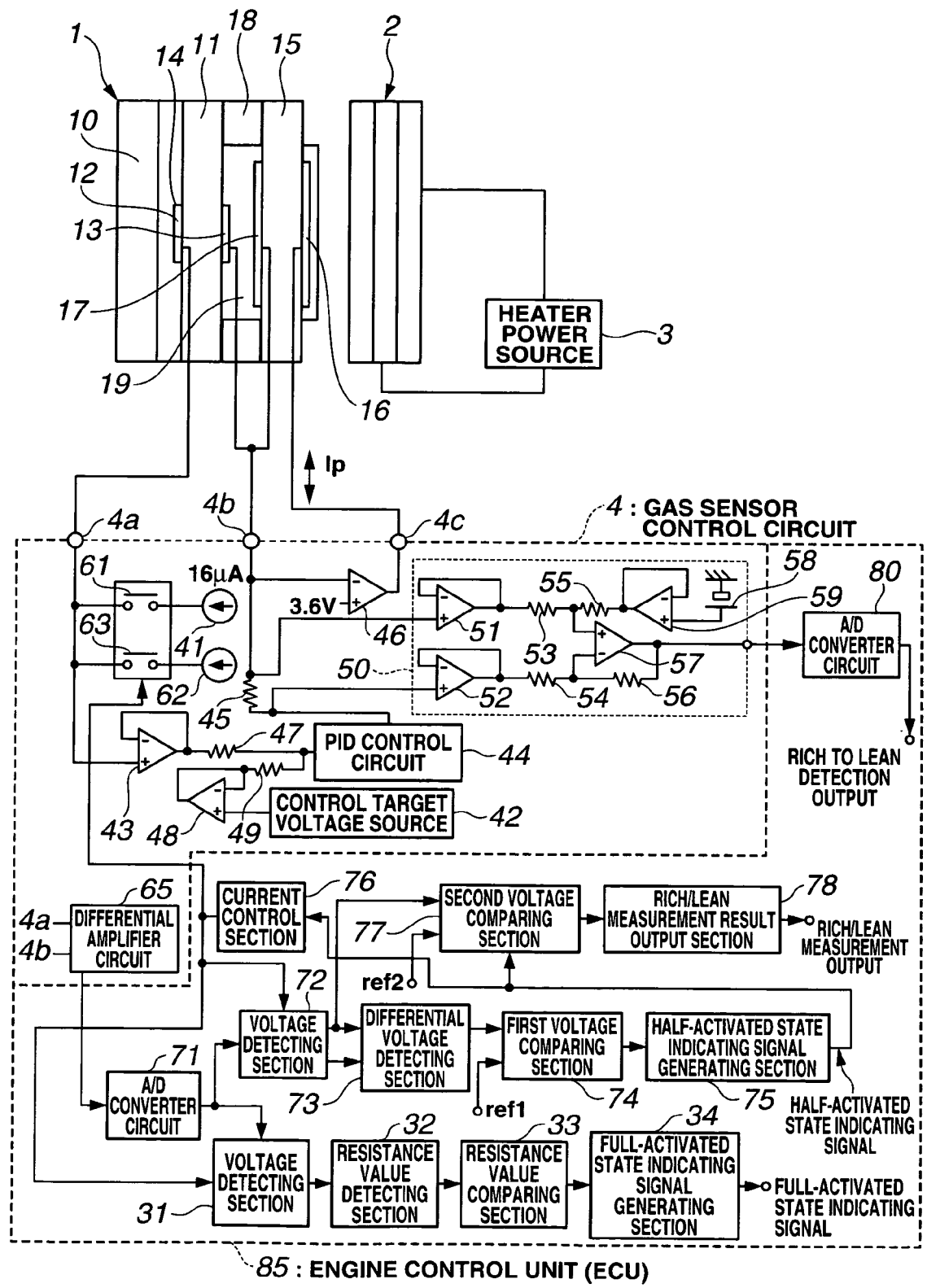
FIG. 1 is a block diagram showing a sensor control apparatus according to an embodiment of the present invention.

Referring first to FIG. 1, a sensor control apparatus according to an embodiment of the present invention includes a wide range oxygen sensor 1 and a gas sensor control circuit 4 connected to the sensor 1. The wide range oxygen sensor 1 has, for heating thereof, a heater 2 that is driven by a heater power source 3. The gas sensor control circuit 4 includes a circuit for controlling the wide range oxygen sensor 1 and a processing system, and generally further includes another structure not shown in the figure. However, the gas sensor control circuit 4 is herein shown so as to include only a portion necessary for explanation of this invention. In the meantime, the wide range oxygen sensor 1 can detect an exhaust gas oxygen concentration over a wide range when being put in a full-activated state and is equivalent to an air/fuel ratio sensor having such output current characteristics that the output current of the sensor is nearly proportional to the air/fuel ratio as will be described hereinafter.

The wide range oxygen sensor 1 includes a shielding plate 10, a solid electrolytic layer 11, a pair of porous electrodes 12 and 13, an reference oxygen chamber 14, another solid electrolytic layer 15, another pair of porous electrodes 16 and 17, a gas diffusion chamber 14 and a gas detecting chamber 19.

On one side of the shielding plate 10 is positioned the reference oxygen chamber 14. On the side of the reference oxygen chamber 14 opposite to the shielding plate 10 is positioned the solid electrolytic layer 11. On the side of the solid electrolytic layer 11 opposite to the reference oxygen chamber 14 are positioned a porous gas diffusion rate control layer 18 and a hollow gas detecting chamber 19. On the side of the gas diffusion rate control layer 18 and the gas detecting chamber 19 opposite to the solid electrolytic layer 11 is positioned the solid electrolytic layer 15. On the opposite sides of the solid electrolytic layer 11 are disposed the pair of porous electrodes 12 and 13, respectively. On the opposite sides of the solid electrolytic layer 15 are disposed the pair of porous electrodes 16 and 17, respectively.

The solid electrolytic layers 11 and 15 are formed of, for example, zirconia ($ZrO_2$) and exhibits, when heated by a heater and put into an activated state, such a nature of being reduced in the internal resistance value and allowing oxygen ion to be movable. For some time hereinafter, description is made when the wide range oxygen sensor 1 is, of variously activated states, in a full-activated state.

An assembly of the solid electrolytic layer 11 and the porous electrodes 12 and 13 on the opposite sides thereof is called an electromotive force cell or sensor cell to which is supplied by an electromotive force cell current source 41 a constant microcurrent (e.g., 16 μA) in the direction to flow from the porous electrode 12 to the porous electrode 13. By this, oxygen is caused to move from the gas detecting chamber 19 to the reference oxygen chamber 14 that is closed to the outside, through the solid electrolytic layer 11, so that reference oxygen is collected at the reference oxygen chamber 14. In this connection, the porous electrode 12 is disposed in the reference oxygen chamber 14 and adapted to serve as a reference electrode. Namely, the porous electrode 12 is closed to the outside and capable of storing oxygen of a predetermined concentration and thereby functioning as an internal reference oxygen source when a microcurrent is supplied between the porous electrodes 12 and 13 as described above. Thus, when the oxygen concentration differs at the opposite sides of the solid electrolytic layer 11, an electromotive force is generated between the porous electrode 12 and 13.

When the oxygen concentration in the gas detecting chamber 19 corresponds to the stoichiometric air/fuel ratio, the electromotive force cell becomes nearly equal to 450 mV for the nature of the solid electrolytic layer 11, and when the oxygen concentration differs from that corresponding to the stoichiometric air/fuel ratio, the electromotive force is saturated at a voltage higher or lower than 450 mV.

While the gas detecting chamber 19 is separated from a space supplied with the exhaust gas by means of the gas diffusion rate control layer 18, the exhaust gas is introduced by diffusion into the gas detecting chamber 19.

An assembly of the solid electrolytic layer 15 and the porous electrodes 16 and 17 is called a pump cell, and a pump cell current (Ip) is supplied to flow between the electrodes 16 and 17 by a PID control circuit 44 and an amplifier 46. More specifically, when an output voltage (generated voltage) of the electromotive force cell is inputted to the PID control circuit 44 by way of a buffer provided by an operational amplifier circuit 43 and a resistor 47, the difference ΔVs between a control target voltage of 450 mV (the control target voltage is equal to the voltage of a control target voltage source 42 and is introduced to the PID control circuit 44 by way of a buffer provided by an operational amplifier circuit 48 and a resistor 49) and the output voltage of the electromotive force cell is PID-calculated by the PID control circuit 44. By feeding the difference ΔVs back to the amplifier 46 by way of a pump cell current detection resistor 45 which will be described later, the pump cell current (Ip) is caused to flow between the porous electrodes 16 and 17. When the pump cell current (Ip) flows through the pump cell, movement of oxygen in the direction in which the current flows is caused between the space supplied with the exhaust gas and the gas detecting chamber 19 by way of the solid electrolytic layer 15.

This movement of oxygen, as will be understood from the foregoing description, is made in either of the directions so that the oxygen concentration in the gas detecting chamber 19 corresponds to the stoichiometric air/fuel ratio. Thus, if the oxygen concentration in the space supplied with the exhaust gas corresponds to the stoichiometric air/fuel ratio, movement of oxygen at the solid electrolytic layer 15 is not necessitated so that the pump cell current becomes zero. If the oxygen concentration in the space supplied with the exhaust gas becomes different from that corresponding to the stoichiometric air/fuel ratio, the pump cell current is generated to flow in either of the directions responsively. Thus, the pump cell current corresponds to the oxygen concentration (i.e., exhaust gas air/fuel ratio) in the space supplied with exhaust gas. Accordingly, by detecting the pump cell current, it becomes possible to measure the oxygen concentration of the exhaust gas over a wide range thereof. Namely, the pump cell has such output characteristics that the pump cell current is nearly proportional to the oxygen concentration (air/fuel ratio) of the exhaust gas.

The gas sensor control circuit 4 has input/output terminals 4a, 4b, 4c and is electrically connected to the wide range oxygen sensor 1. The functions of the electromotive force cell current source 41, the control target current source 42, the amplifier 46, the operational amplifier circuits 43 and 38, and the resistors 47 and 49 will be understood from the foregoing description and therefore repeated description thereto is omitted for brevity, but they function as a part of the sensor control apparatus for controlling the wide range oxygen sensor 1 as described above.

Review of their connection relationships being made, as shown in FIG. 1, the amplifier 46 has a reverse input terminal connected with an output side of the PID control circuit 44 by way of the detection resistor 45, a non-reverse input terminal to which a reference voltage of 3.6 V is applied and an output terminal connected to the input terminal 4c. Further, the PID control circuit 44 is connected at the input side to the input/output terminal 4a by way of the resistor 47 and the operational amplifier circuit 43 and at the output side to a reverse input terminal of the amplifier 46 by way of the pump cell current detection resistor 45. Further, the control target voltage source 42 supplies voltage (450 mV) that is a control target for controlling the pump cell current to the PID control circuit 44 by way of the operational amplifier circuit 48 and the resistor 49. At the gas sensor control circuit 4, detection of the pump cell current (Ip) is made by using the pump cell current detection resistor 45 disposed in series to the output side of the PID control circuit 44 and connected at an end to the input/output terminal 4b.

A first switch 61 connected in series to the electromotive force cell current source 41 is turned on by the instruction of a current control section 76 when the wide range oxygen sensor 1 is in a full-activated state.

Detection of the pump cell current (IP) will be described. For detecting the voltage across the pump cell current detection resistor 45, a pump cell current detection circuit 50 is provided as shown. The pump cell current detection circuit 50 includes operational amplifier circuits 51 and 52, resistors 53, 54, 55 and 56, an operational amplifier circuit 57, a detection reference voltage source 58 and an operational amplifier circuit 59.

The operational amplifier circuits 51 and 52 are provided for buffering the voltage across the pump cell current detection resistor 45 and introducing it to a differential amplifier section in the next step. For this reason, the operational amplifier circuits 51 and 52 are used as voltage follower circuits. The resistors 53, 54, 55, 56 and the operational amplifier circuit 57 constitute a differential amplifier section. Namely, one end of the resistor 53 is an input terminal of one pole and one end of the resistor 54 is an input terminal of the other pole. The amplification factor from one pole is defined by the resistance value of the resistor 55/the resistance value of the resistor 53, and the amplification factor from the other pole is defined by the resistance value of the resistor 56/the resistance value of the resistor 54. These factors are generally set equal to each other.

The detection reference voltage source 58 and the operational amplifier circuit 59 determine a reference voltage for the output of the above-described differential amplifier section, i.e., a reference voltage for the output of the pump cell current detection circuit 50, and the voltage of the detection reference voltage source 58 becomes the output reference voltage of the pump cell current detection circuit 50. The above-described amplification factor and output reference voltage can be designed or set suitably in accordance with the details of the processing carried out in the following stage. The pump cell current detection circuit 50 outputs, on the basis of the voltage of the detection reference voltage source 50, a voltage corresponding to the pump cell current.

The output of the pump cell current detection circuit 50 is supplied to an A/D converter circuit 80 within an ECU 85 and converted to a digital signal. The digital signal thus obtained by conversion is used as a detection or measurement output representative of an air/fuel ratio over a wide range from rich to lean in the following processing executed by the ECU 85. Namely, though not shown, by feedback of the measurement output, a desired air/fuel ratio feedback control for controlling an amount of fuel to be supplied is carried out.

The foregoing description is made with respect to a control that is carried out after the wide range oxygen sensor 1 has reached a full-activated state, i.e., a control in a normal case. Actually, unless the wide range oxygen sensor 1 is put into a state of being fully heated by the heater 2, an air/fuel ratio feedback control using the detection output outputted from the A/D converter circuit 80 after the PID control circuit 44 and the amplifier 46 are driven, cannot be carried out.

With a view to making up for such a state where the air/fuel ratio feedback control cannot be carried out, the sensor control apparatus of this invention is provided with a processing system capable of detecting whether the air/fuel ratio of the exhaust gas is richer or leaner as compared with the stoichiometric air/fuel ratio (i.e., capable of producing a binary output). By using such a binary information, i.e., an information whether the air/fuel ratio is rich or lean, in the air/fuel ratio feedback control, an earlier or accelerated air/fuel ratio feedback control after start of the internal combustion engine can be realized.

To this end, the ECU 85 connected to the gas sensor control circuit 4 further includes an A/D converter circuit 71, a voltage detecting section 72, a differential voltage detecting section 73, a first voltage comparing section 74, a half-activated state indicating signal generating section (half-activated state determining section) 75, a current control section 76, a second voltage comparing section 77, a rich/lean measurement result output section 78, a voltage detecting section 31, a resistance value detecting section 32, a resistance value comparing section (full-activated state determining section) 33 and a full-activated state indicating signal generating section 34.

The A/D converter circuit 71 is supplied with the output voltage (Vs) generated between the pair of electrodes of the electromotive force cell of the wide range oxygen sensor 1 by way of a differential amplifier circuit 65 and converts it to a digital signal. In the meantime, the differential amplifier circuit 65 is provided for outputting the potential difference between the pair of electrodes of the electromotive force cell to the A/D converter circuit 71 and has input terminals connected to the input/output terminals 4a, 4b, respectively though connecting lines for this end are omitted in FIG. 1. The digital signal thus obtained by the A/D converter circuit 71 is supplied to the voltage detecting section 72. The voltage detecting section 72 detects the voltage of digital value at two timings (on and off timings) instructed by the current control section 76. Detected voltage values are supplied to the differential voltage detecting section 73. The differential voltage detecting section 73 obtains a differential voltage between the voltage values. The differential voltage obtained by the differential voltage detecting section 73 is supplied as one input to the first voltage comparing section 74. The first voltage comparing section 74 compares the differential voltage supplied from the differential voltage detecting section 73 with a reference voltage (first threshold voltage) ref1. The result of the comparison is supplied to the half-activated state indicating signal generating section 75.

The half-activated state indicating signal generating section 75 outputs a signal indicative of the half-activated state of the wide range oxygen sensor 1, on the basis of the result of comparison obtained from the first voltage comparing section 74. In this connection, "half-activated state" is herein used to indicate that the wide range oxygen sensor 1 is in a state of being capable of generating a binary detection output, i.e., an output indicating rich or lean. The indication signal generated by the half-activated state indicating signal generating section 75 is supplied to the second voltage comparing section 77 as an enable signal.

The current control section 76 controls on/off switching of the first switch 61 and generates a signal indicative of the timing of operation of the voltage detecting section 72. The on/off switching of the first switch 61 is performed repeatedly at a predetermined cycle until the half-activated state indicating signal generating section 75 determines that the wide range oxygen sensor 1 has reached the half-activated state (i.e., until a signal indicative of a half-activated state is inputted to the current control section 76. In the meantime, the second switch 63 which will be described later is controlled so as to be turned off until the signal indicative of the half-activated state is inputted to the current control section 76. Further, the first switch 61 is set so as to be turned on after the wide range oxygen sensor 1 has reached the full-activated state.

After the wide range oxygen sensor 1 has reached the half-activated state, the current control section 76 executes a process of switching the second switch 63 from off to on every time a predetermine time elapses. The switching of the second switch 63 from off to on every time a predetermined time elapses is performed until the wide range oxygen sensor 1 reaches the half-activated state.

The signal supplied from the current control section 76 to the voltage detecting section 72 is a timing signal corresponding to each timing at which the first switch 61 is turned on or off. The signal supplied from the current control section 76 to the voltage detecting section 31 is a timing signal corresponding to the timing at which the second switch 63 is switched from off to on.

The second voltage comparing section 77 receives as one input the voltage outputted by the voltage detecting section 72 when the first switch 61 is on and compares it with the reference voltage ref2 (in this connection, the half-activated state indicating signal is outputted as an enable signal of comparison operation). The result of comparison is supplied to the rich/lean measurement result output section 78. The rich/lean measurement result output section 78 outputs a signal indicating whether the air/fuel ratio of the exhaust gas supplied to the wide range oxygen sensor 1 is rich or lean on the basis of the result of the comparison obtained from the second voltage comparing section 77. This output is used for a process thereafter executed by the ECU 85, though not shown, such that an amount of fuel to be supplied thereafter is controlled to realize an earlier or accelerated air/fuel ratio feedback control. In the meantime, since the first switch 61 is held in a state of being turned on continuously until the wide range oxygen sensor 1 reaches the full-activated state after having reached the half-activated state, the second voltage comparing section 77 compares the voltage outputted by the voltage comparing section 72 with the reference voltage (second threshold voltage) ref2, supplies the result of the comparison to the rich/lean measurement result output section 78 and outputs a signal indicating whether the air/fuel ratio of the exhaust gas is rich or lean to the ECU 85.

The voltage detecting section 31 detects the voltage (potential difference) generated between the pair of electrodes of the electromotive force cell by way of the A/D converter circuit 71 when the second switch 63 is on, and the resistance value detecting section 32 detects, on the basis of the voltage, the internal resistance value of the electromotive force cell of the wide range oxygen sensor 1. The resistance value comparing section 33 determines whether the internal resistance value of the electromotive force cell, which is detected by the resistance value detecting section is lower than a predetermined threshold resistance value and supplies, when it is determined that the internal resistance value of the electromotive force cell has become lower than the threshold resistance value, a signal indicative thereof to the full-activated state indicating signal generating section 34. The full-activated state indicating signal generating section 34 outputs a full-activated state indicating signal.

Figure 2A:
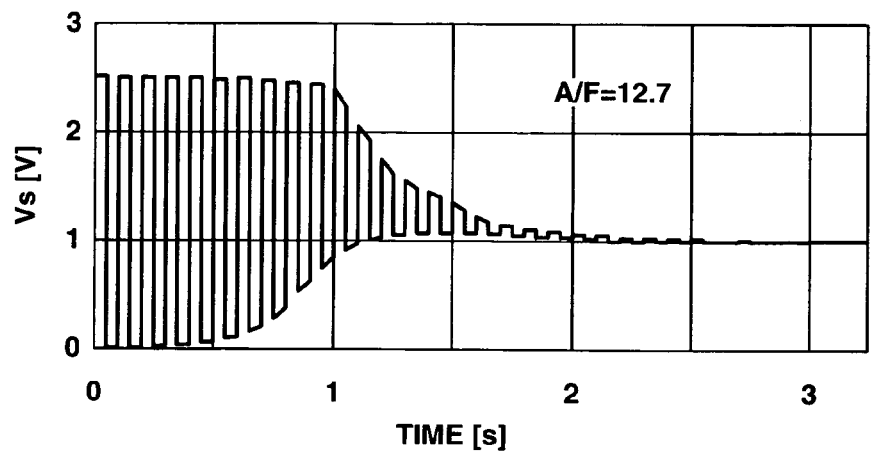
FIGS. 2A to 2C are explanatory views showing variations of output voltage of an electromotive force cell in a wide range oxygen sensor of the sensor control apparatus of FIG. 1.
Figure 2B:
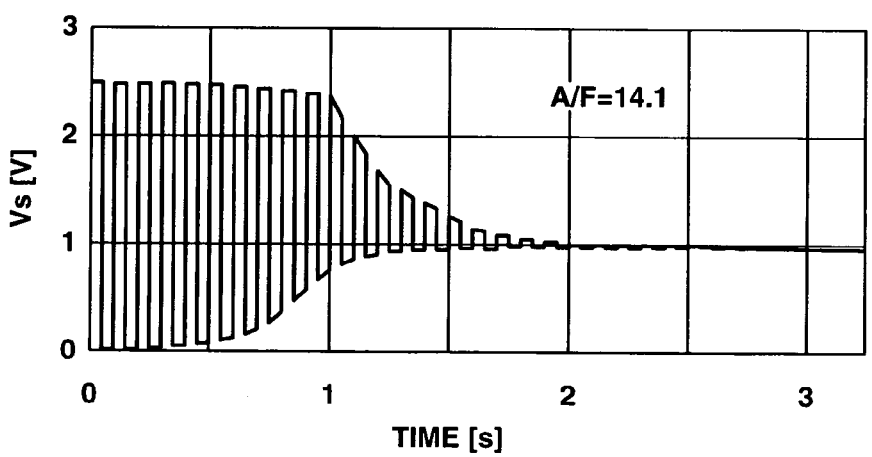
Figure 2C:
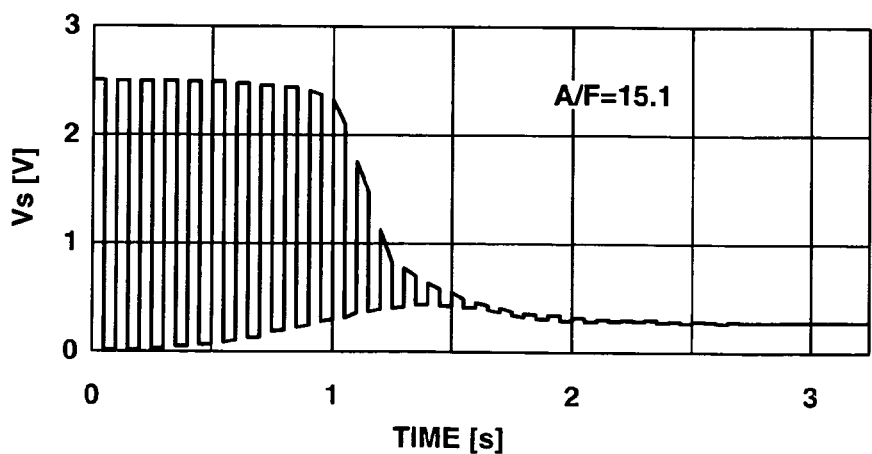

FIGS. 2A to 2C show a variation of the voltage (Vs) generated by the electromotive force cell at start of the internal combustion engine and correspond to gases to be measured (exhaust gases) which are different in air/fuel (A/F) ratio. The cyclic variation in the voltage generated by the electromotive force cell, which is shown in the figures, is caused by on/off switching of the first switch 61. In this instance, on/off switching of the first switch 61 is performed at duty ratio of 50% and 10 Hz.

The reason why the amplitude at the beginning of start (amplitude represents the differential voltage for the wide range oxygen sensor 1 when the electromotive force cell current supply current source 41 is on or off and is referred to as "differential voltage" in the description with reference to FIG. 1) is large is that the wide range oxygen sensor 1 is in a non-activated state and the solid electrolytic layer 11 exhibits a high resistance value. The amplitude becomes smaller as the solid electrolytic layers 11 and 15 are heated to become smaller in the resistance value (i.e., with lapse of time).

Figure 3:
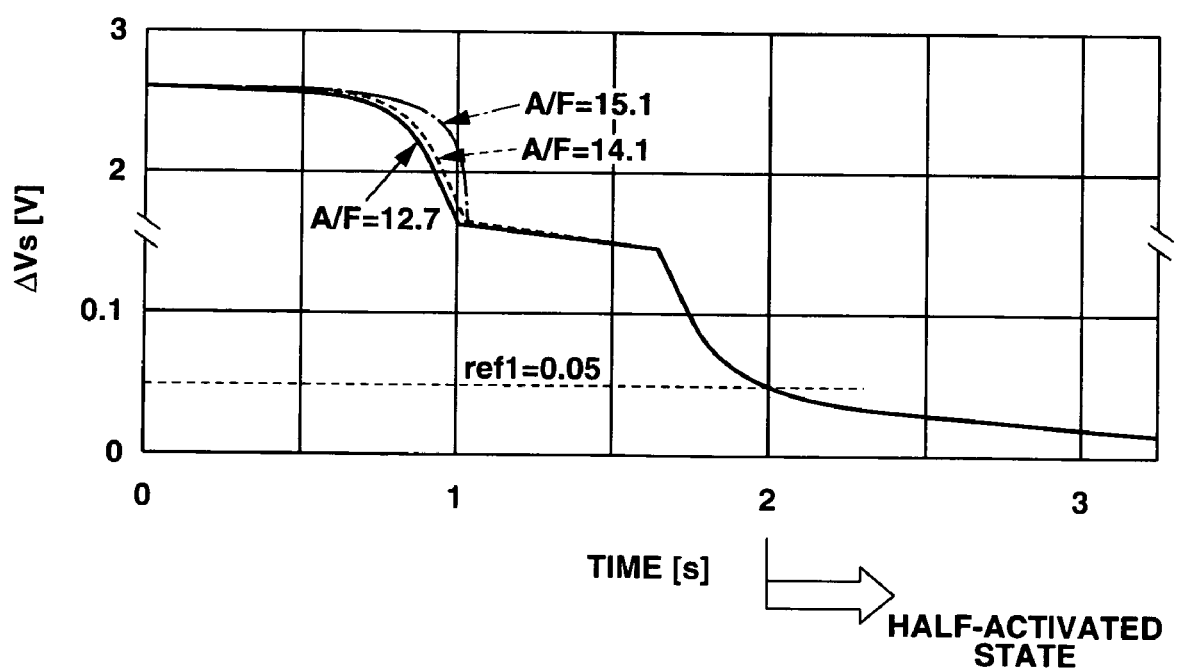
FIG. 3 is an explanatory view showing, by using an amplitude Vs, the variations of voltage shown in FIGS. 2A to 2C.

FIG. 3 shows the voltage variation in FIG. 2 by an amplitude value (ΔVs). As shown in FIG. 3, decrease in the amplitude value with lapse of time is constant irrespective of a variation of the air/fuel ratio. Accordingly, whatever air/fuel ratio the gas to be measured (exhaust gas) may have, it can be known how much the solid electrolytic layer 11 is activated by looking up the amplitude with a predetermined criterion. When the amplitude value ΔVs becomes lower than 0.05V, it is herein determined that the solid electrolytic layer 11 has reached the half-activated state. This corresponds to that the reference voltage ref1 supplied to the voltage comparing section 74 in the circuit of FIG. 1 is 0.05V. As shown in FIG. 3, in this case, the wide range oxygen sensor 1 has reached the half-activated state in two seconds after start of the internal combustion engine.

Figure 4A:
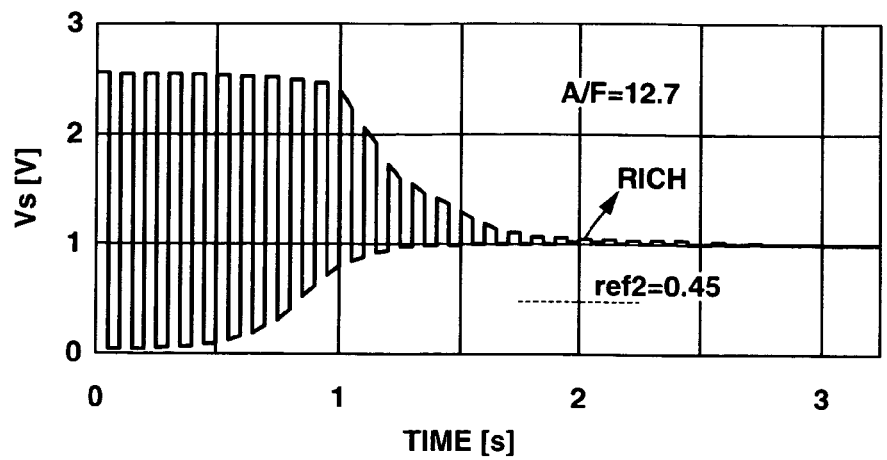
FIGS. 4A to 4C are explanatory views showing rich/lean determination in relation to the voltage variations shown in FIGS. 2A to 2C.
Figure 4B:
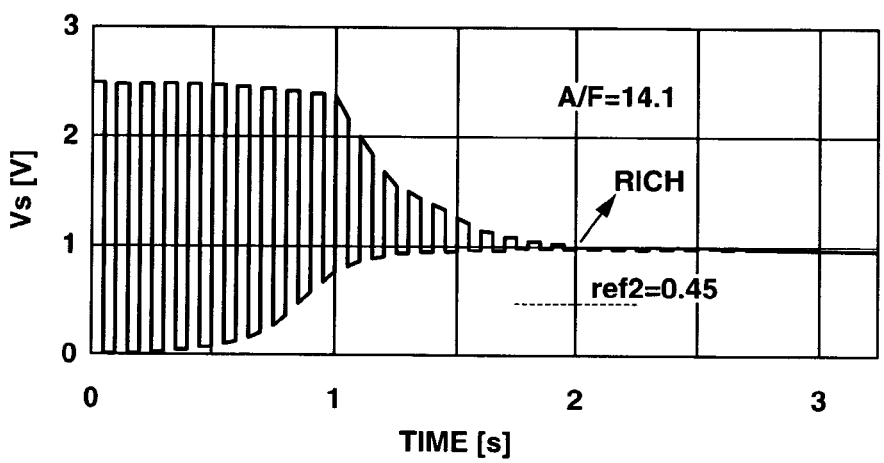
Figure 4C:
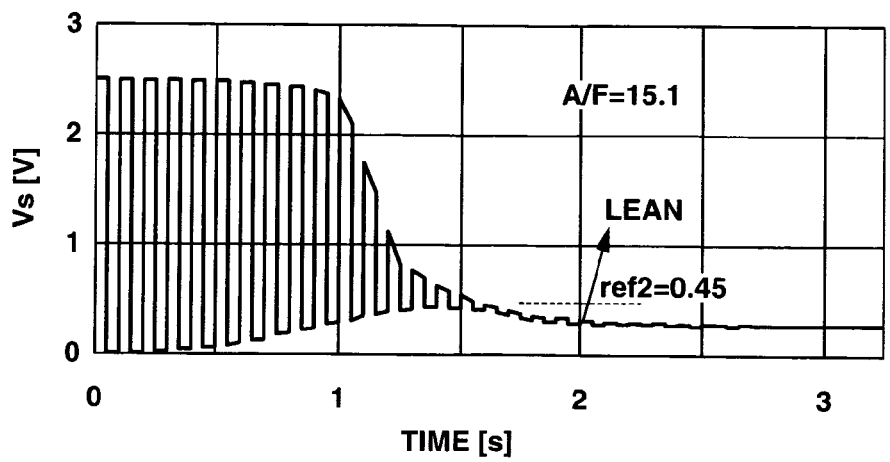

FIGS. 4A to 4C show rich/lean determination in relation to voltage variations in FIGS. 2A to 2C and are exactly the same as FIGS. 2A to 2C except for addition of written expressions relating to the determination.

If as shown in FIG. 3, the wide range oxygen sensor 1 has reached the half-activated state in two seconds after start of the internal combustion engine, it can then be determined by comparing the voltage Vs generated by the electromotive force cell when the electromotive force cell is supplied with current by the electromotive force cell current source 41 with the reference voltage ref2 whether the exhaust gas corresponds to a rich air/fuel ratio or lean air/fuel ratio. In this instance, the reference voltage ref2 is fixed to 0.45V. By this, it can be determined from the voltage Vs generated by the electromotive force cell in two seconds after start of the engine that the air/fuel ratio is rich in cases of FIGS. 4A and 4B and lean in case of FIG. 4C. In this connection, the reference voltage ref2 corresponds to the voltage ref2 supplied to the second voltage comparing section 77 in FIG. 1.

The reason why the reference voltage ref2 is fixed to 0.45V is that the voltage of the electromotive force cell is controlled so as to be 0.45V when the wide range oxygen sensor 1 is in the full-activated state. This has already been described hereinbefore. Though in two seconds after start of the engine in FIGS. 4A to 4C a complete operation of the wide range oxygen sensor 1 in the full-activated state (normal operation) has not yet been obtained, it is shown by the figures that the electromotive force cell has generated voltages corresponding to the respective exhaust gases as the result of diffusion of the exhaust gases into the gas detecting chamber 19. In the meantime, while the air/fuel ratio A/F=14.1 in FIG. 4B corresponds to that at or adjacent the stoichiometric air/fuel ratio, the result of determination in this instance is rich. Such determination may possibly be caused since it is an object at this moment to obtain a binary output of rich/lean.

Figure 5:
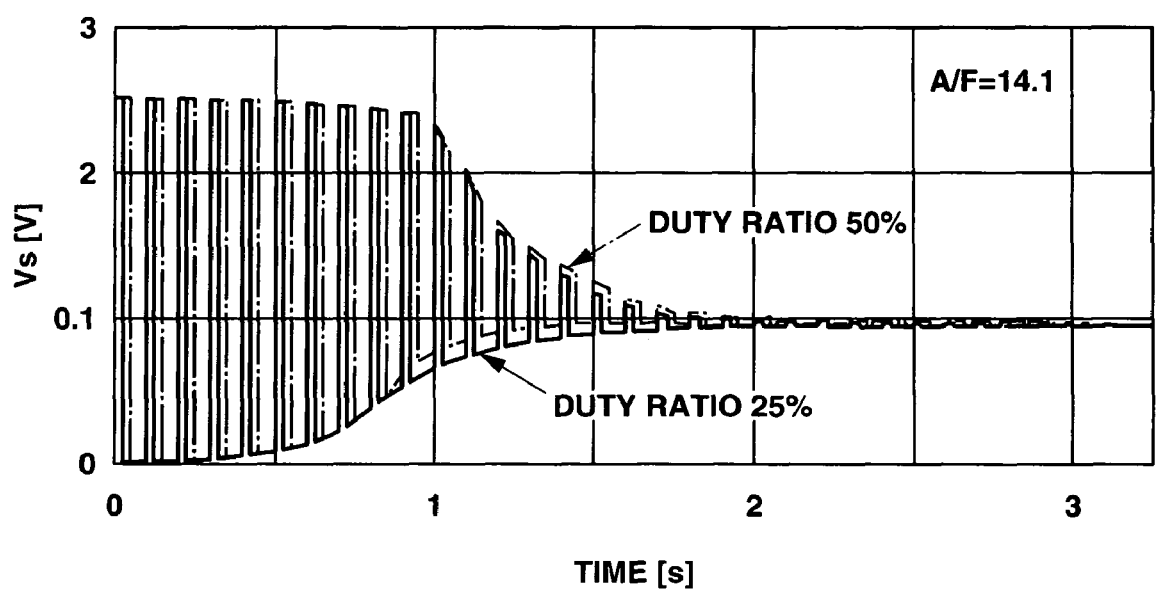
FIG. 5 is an explanatory view showing influence of drive duty ratio on the voltage variations shown in FIG. 2B.

FIG. 5 shows influence of drive duty ratio on the voltage variation shown in FIG. 2B. The drive duty ratio is a ratio of a working time for turning on the first switch 61 to a total time for one switching cycle. As shown in FIG. 5, it was found that by decreasing the drive duty ratio to 25% the voltage Vs of the electromotive force cell, that was outputted as a whole, was lowered. However, it was also found that such lowering of the voltage Vs did not cause any influence on the determination of the half-activated state shown in FIG. 3 and the rich/lean determination shown in FIG. 4. Accordingly, the drive duty ratio is not limited to 50% but can be selectively set at a suitable value by conducting such examination as described above.

While all the description as to the structure and operation of the apparatus and the wide range oxygen sensor 1 has been made in the foregoing, the processing to be executed, for example, after the A/D converter circuit 71 shown in FIG. 1 is a digital processing and therefore can be of course a software processing by means of a microprocessor. In such a case, selection can be made so that the processing by a microprocessor is executed after the process by the differential voltage detecting section 73 and the second voltage comparing section 77 or after the process by the second voltage comparing section 77 only.

FIG. 6 is a flowchart of the operation of the sensor control apparatus shown in FIG. 1 in case all the processing after the A/D converter circuit 71 is performed by a software processing by a microprocessor. In this case, the above-described structures of the voltage detecting section 72, first voltage comparing section 74, half-activated state indicating signal generating section 78, voltage detecting section 31, resistance value detecting section 32, resistance value comparing section 33 and full-activated state indicating signal generating section 34 are realized by the motion attained by the software operation of the microprocessor. Hereinafter, the flow of operation of the sensor control apparatus will be described.

First, in step 81, the first switch 61 is turned on by the current control section 76 so that the current of the electromotive force cell current source 41 is supplied to the electromotive force cell of the wide range oxygen sensor 1 (i.e., Icp is on). In step 82, under this condition, the voltage Vs generated by the electromotive force cell is detected by the voltage detecting section 72 and the detected voltage is kept in a memory (not shown).

Then, in step 83, the current Icp is off by the current control section 76 after lapse of a predetermined time (after lapse of 50 msec in case of switching at duty ratio 50% and 10 Hz as described above). In step 84, the voltage Vs generated by the electromotive force cell in an off state is detected. In step 85, a differential voltage ΔVs between the detected voltage Vs and the above-described kept voltage Vs is obtained.

In step 86, the differential voltage ΔVs thus obtained is compared with the reference voltage ref1. If the differential voltage ΔVs is not lower than the reference voltage ref1, the program proceeds to step 87 where the current Icp is on again after lapse of the predetermined time. Then, the process at step 82 onward is repeated.

If it is found by the comparison in step 86 that the differential voltage is lower than the reference voltage, it is determined that the wide range oxygen sensor 1 has reached the half-activated state and the program proceeds to the next process. First, in step 88, the first switch 61 is turned on (i.e., current Icp is on). Then, in step 89, the kept voltage Vs is compared with the reference voltage ref2. If the kept voltage Vs is lower than the reference voltage ref2, the program proceeds to step 90 where a signal indicative of "lean" is outputted by the rich/lean measurement result output section 78. If the kept voltage Vs is not lower than the reference voltage ref2, the program proceeds to step 91 where a signal indicative of "rich" is outputted by the rich/lean measurement result outputting section 78.

Then, in step 92, the timer (not shown) is started. The timer is provided for generating a timing at which a process for determining whether the wide range oxygen sensor 1 has reached the full-activated state is executed. For example, it can be a 100 msec timer. In step 93, if lapse of a predetermined time is not detected by the timer, the program proceeds to step 94 where the voltage generated by the electromotive force cell is detected by the voltage detecting section 72 and the detected voltage is kept in the memory. Thereafter, the program returns to step 89 to execute the process onward similarly as described above. In case the program goes to the step 92 again after returning to the step 89, nothing is executed at step 92 (i.e., an operation for starting the timer is executed only for the first time).

In step 93, if it is detected by the timer that the predetermined time has elapsed, the program proceeds to the next process for measuring the internal resistance value of the electromotive force cell of the wide range oxygen sensor 1. First, in step 95, the current source 62 for detection of the electromotive force cell resistance is connected to the electromotive force cell. The current value of the current source 62 for detection of the electromotive force cell resistance is for example 1.22 mA. In step 96, under this condition, the voltage Vs of the electromotive force cell is detected by the voltage detecting section 31 and the internal resistance value is obtained from the voltage Vs. Then, in step 97, the second switch 63 is turned off by the current control section 76 to disconnect between the current source 62 for detection of the electromotive force cell resistance and the electromotive force cell.

Then, in step 98, the thus obtained internal resistance value of the electromotive force cell is compared with a threshold resistance value Rth. If the obtained internal resistance value is lower than the threshold resistance value Rth, the program proceeds to step 99 where it is determined that the wide range oxygen sensor 1 has reached the full-activated state and a signal indicative thereof is outputted by the voltage detecting section 31. By this, the process is ended. In the meantime, the threshold resistance value Rth can be set at 220Ω for instance.

If it is determined in step 98 that the internal resistance value of the electromotive force cell is not lower than the threshold resistance value Rth, the program proceeds to step 100 where the timer is restarted to obtain the timing for next measurement of the resistance value and the process in step 93 onward is executed again. After the wide range oxygen sensor 1 has reached the full-activated state, the PID control circuit 44 and the amplifier 46 shown in FIG. 1 are driven to execute a complete air/fuel ratio feedback control by means of an output signal of the pump cell current detecting circuit 50 as having been already described. When the wide range oxygen sensor 1 is in the half-activated state before reaching the full-activated state, an air/fuel ratio feedback control of the internal combustion engine is executed on the basis of the output of the rich/lean measurement result output section 78.

In the meantime, while in the flowchart of the operation of the sensor control apparatus, it has been described and shown a structure in which a signal indicative of whether the air/fuel ratio of the exhaust gas is rich or lean is outputted on the basis of the result of comparison between the voltage detected when the current Icp is on and the reference voltage ref2, this is not for the purpose of limitation. For example, the flowchart can be modified so that a signal indicative of whether the air/fuel ratio of the exhaust gas is rich or lean is outputted on the basis of the result of comparison between the voltage Vs detected when the current Icp is off and the reference voltage ref2. More specifically, the flowchart can be modified in a way as to replace step 82 and step 84 with each other, cancel the processing of the step 88, introduce a step for turning the first switch 61 on after affirmative determination in step 98, and then allow the control to go to step 99.

The entire contents of Japanese Patent Applications P2005-264879 (filed Sep. 13, 2005) are incorporated herein by reference.

Although the invention has been described above by reference to a certain embodiment of the invention, the invention is not limited to the embodiment described above. Modifications and variations of the embodiment described above will occur to those skilled in the art, in light of the above teachings. The scope of the invention is defined with reference to the following claims.

What is claimed is:

1. A sensor control apparatus comprising:
   an air/fuel ratio sensor having a sensor cell with a pair of electrodes on opposite sides of a solid electrolyte and capable of detecting a concentration of a particular gas component of an exhaust gas emitted from an internal combustion engine;
   a current source capable of supplying a predetermined current between the pair of electrodes; and
   a control unit comprising:

a current control section that turns on/off the current source at a predetermined cycle;

a voltage detecting section that detects voltages generated between the pair of electrodes at respective times when the current source is turned on and off;

a differential voltage detecting section that calculates a differential voltage between the voltages that are generated at the respective times when the current source is turned on and off and detected by the voltage detecting section;

a first voltage comparing section that compares the differential voltage with a first threshold voltage;

a half-activated state determining section that determines that the sensor cell has reached a half-activated state that enables the air/fuel ratio sensor to measure whether an air/fuel ratio of the exhaust gas is rich or lean on the basis of an output of the sensor cell, when the differential voltage is lower than the first threshold voltage;

a second voltage comparing section that compares, when it is determined by the half-activated state determining section that the sensor cell has reached the half-activated state, a voltage between the pair of electrodes, which is detected by the voltage detecting section when the current source is on or off, with a second threshold voltage that is different than the first threshold voltage;

a rich/lean measurement result output section that outputs a signal indicative of the air/fuel ratio of the exhaust gas being rich or lean on the basis of the result of comparison by the second voltage comparing section;

a full-activated state determining section that determines whether the sensor cell has reached a full-activated state on the basis of information that is different from the differential voltage after it is determined by the half-activated state determining section that the sensor cell has reached the half-activated state;

wherein the full-activated state determining section uses an internal resistance value of the sensor cell as said information; and a resistance value detecting section that detects the internal resistance value of the sensor cell, wherein the full-activated state determining section compares the internal resistance value of the sensor cell with a threshold value and determines that the sensor cell has reached the full-activated state when the internal resistance value is lower than the threshold value.

2. A sensor control apparatus according to claim 1, wherein the air/fuel ratio sensor further includes a pump cell having a pair of electrodes on opposite sides of a solid electrolyte, one of the electrodes of each of the pump cell and the sensor cell facing a gas detecting chamber into which the exhaust gas is introduced, one of the electrodes of the sensor cell, which is positioned on a side opposite to the gas detecting chamber, being a reference electrode closed to the outside, the sensor control apparatus further comprising a control section that supplies a predetermined current from the current source to the sensor cell in the direction to pump oxygen out of the gas detecting chamber to the reference electrode for thereby allowing the reference electrode to function as an internal reference oxygen source.

3. A sensor control apparatus according to claim 1, wherein the resistance value detecting section detects the internal resistance value based on the voltages detected by the voltage detecting section.

4. A sensor control method for controlling an air/fuel ratio sensor having a sensor cell with a pair of electrodes on opposite sides of a solid electrolyte and capable of detecting a concentration of a particular gas component of an exhaust gas emitted from an internal combustion engine, the method comprising the steps of:

supplying a predetermined current of a current source between the pair of electrodes while turning on/off the current source at a predetermined cycle;

detecting voltages generated between the pair of electrodes at respective times when the current source is turned on and off;

calculating a differential voltage between the voltages that are generated between the pair of electrodes at the respective times when the current source is turned on and off and detected by the step of detecting;

comparing the differential voltage with a first threshold voltage;

determining that the sensor cell has reached a half-activated state that enables the air/fuel ratio sensor to measure whether an air/fuel ratio of the exhaust gas is rich or lean on the basis of an output of the sensor cell, when the differential voltage is lower than the first threshold voltage;

comparing, when it is determined by determining step that the sensor cell has reached the half-activated state, a voltage generated between the pair of electrodes when the current source is on or off, with a second threshold voltage that is different than the first threshold voltage;

outputting a signal indicative of whether the air/fuel ratio of the exhaust gas is rich or lean, on the basis of the result of the step of comparing the voltage between the pair of electrodes with the second threshold voltage;

determining whether the sensor cell has reached a full-activated state on the basis of information that is different from the differential voltage after it is determined by the step of determining that the sensor cell has reached the half-activated state;

wherein the step of determining whether the sensor cell has reached the full-activated state comprises using an internal resistance value of the sensor cell as said information; and detecting an internal resistance value of the sensor cell, wherein the step of determining whether the sensor cell has reached the full-activated state comprises comparing the internal resistance value of the sensor cell with a threshold value and determining that the sensor cell has reached the full-activated state when the internal resistance value is lower than the threshold value.

5. A control method according to claim 4, in which the air/fuel ratio sensor further includes a pump cell having a pair of electrodes on opposite sides of a solid electrolyte, one of the electrodes of each of the pump cell and the sensor cell facing a gas detecting chamber into which the exhaust gas is introduced, one of the electrodes of the sensor cell, which is positioned on a side opposite to the gas detecting chamber, being a reference electrode closed to the outside, the sensor control method further comprising supplying the predetermined current of the current source to the sensor cell in the direction to pump oxygen out of the gas detecting chamber to the reference electrode for thereby allowing the reference electrode to function as an internal reference oxygen source.

6. A control method according to claim 4, wherein the internal resistance value is detected based on the detected voltages.

* * * * *